United States Patent
Carrasco (10) Patent No.: US 11,432,897 B2
(45) Date of Patent: Sep. 6, 2022

(54) NEONATAL DRAPE DEVICE

(71) Applicant: A.T. Still University, Kirksville, MO (US)

(72) Inventor: Noel J. M. Carrasco, Mesa, AZ (US)

(73) Assignee: A.T. STILL UNIVERSITY, Kirksville, MO (US)

( * ) Notice: Subject to any disclaimer, the term of this patent is extended or adjusted under 35 U.S.C. 154(b) by 628 days.

(21) Appl. No.: 15/277,303

(22) Filed: Sep. 27, 2016

(65) Prior Publication Data

US 2018/0085249 A1 Mar. 29, 2018

(51) Int. Cl.
| | |
|---|---|
| *A61F 7/02* | (2006.01) |
| *A61B 46/23* | (2016.01) |
| *A61B 46/00* | (2016.01) |
| *A61B 46/20* | (2016.01) |
| *A61F 7/00* | (2006.01) |

(52) U.S. Cl.
CPC .............. *A61B 46/23* (2016.02); *A61B 46/20* (2016.02); *A61B 46/40* (2016.02); *A61B 2046/205* (2016.02); *A61F 7/02* (2013.01); *A61F 2007/0054* (2013.01); *A61F 2007/0226* (2013.01)

(58) Field of Classification Search
CPC ................ A61F 7/02; A61F 2007/0054; A61F 2007/0056; A61F 2007/0057; A61B 46/20; A61B 46/40; A41B 13/06
See application file for complete search history.

(56) References Cited

U.S. PATENT DOCUMENTS

| | | | |
|---|---|---|---|
| 3,636,566 A | | 1/1972 | Sutherland |
| 3,739,399 A | * | 6/1973 | Sheahon .............. A41B 13/06 2/69.5 |
| 3,854,156 A | | 12/1974 | Williams |
| 4,083,064 A | | 4/1978 | Schneider |
| 5,852,827 A | | 12/1998 | Lear |
| 5,891,187 A | * | 4/1999 | Winthrop ................ A61F 7/00 126/204 |
| 6,228,106 B1 | | 5/2001 | Simbruner et al. |

(Continued)

FOREIGN PATENT DOCUMENTS

| | | | |
|---|---|---|---|
| EP | 2543269 A1 | 1/2013 | |
| GB | 1462033 A * | 1/1977 | ............... A61F 7/02 |

(Continued)

OTHER PUBLICATIONS

PCT International Search Report and Written Opinion, PCT/US2017/053454, dated Dec. 7, 2017.

*Primary Examiner* — Tigist S Demie (74) *Attorney, Agent, or Firm* — Quarles & Brady LLP (57) ABSTRACT

A neonatal drape device for protecting a neonatal subject comprising a sheet configured to receive the neonatal subject in a supine position. The sheet has a base, at least one side edge, and a plurality of separation lines. The separation lines extend inwardly from the at least one side edge of the sheet. The sheet is sufficiently pliable so as to wrap and conform to the neonatal subject. The sheet further includes a plurality of notches disposed adjacent to the base, each at an inner end of one of the separation lines. The notches are configured to allow a cable to extend from an internal space of the neonatal drape device to an external location while the sheet is wrapped around the neonatal subject.

20 Claims, 7 Drawing Sheets

(56) References Cited

U.S. PATENT DOCUMENTS

| | | | |
|---|---|---|---|
| 6,371,976 B1* | 4/2002 | Vrzalik | A61F 7/0097 5/606 |
| 8,191,188 B2 | 6/2012 | Kaplan et al. | |
| 8,607,364 B2 | 12/2013 | Barski | |
| 9,326,888 B2 | 5/2016 | Chen et al. | |
| 2006/0247745 A1* | 11/2006 | Thompson | A61F 7/02 607/108 |
| 2007/0016271 A1* | 1/2007 | Hammond | A61F 7/007 607/96 |
| 2009/0144875 A1 | 6/2009 | Pearson et al. | |
| 2010/0300459 A1 | 12/2010 | Lair | |
| 2011/0224760 A1* | 9/2011 | Potter | A61F 7/0097 607/104 |
| 2013/0036536 A1 | 2/2013 | Breindahl et al. | |
| 2013/0340770 A1* | 12/2013 | Starr | A47D 15/008 128/870 |
| 2014/0238413 A1 | 8/2014 | Ottinger | |
| 2016/0192792 A1* | 7/2016 | Townsend | A41D 13/0012 5/484 |

FOREIGN PATENT DOCUMENTS

| | | |
|---|---|---|
| WO | 9405238 A1 | 3/1994 |
| WO | 2007141490 A1 | 12/2007 |

* cited by examiner

NEONATAL DRAPE DEVICE

CROSS-REFERENCE TO RELATED APPLICATIONS

Not applicable.

BACKGROUND

This application relates generally to a neonatal drape device for providing thermoregulation to a neonate. Thermoregulation in the neonate has been a concern of health care professionals since at least as early as the 1950s, when it was determined that newborn infants, and particularly those born prematurely, have an increased mortality rate when their body temperature falls below 36° C. The increase in mortality has been associated with hypoglycemia, hypoxemia, metabolic acidosis, increased risk of infection, and alterations in surfactant production which result from heat loss. Therefore, maintenance of body temperature within a narrow range can be critical to the survival and subsequent growth of human infants in general, and specifically to the prematurely born human infant.

The neonatal subject, being born prematurely, is not yet able to regulate its own body temperature. Heat loss in the neonate can occur through at least four mechanisms: conduction (from the body to a solid surface that is in direct contact with the body), convection (from the body to the surrounding air), radiation (from the body to a cool solid object not in direct contact with the body), and evaporation (conversion of moisture to a vapor). It is important, therefore, to keep an infant both warm and moist until it can be placed into an incubator To diminish heat loss through these mechanisms, health care professionals have used a variety of techniques, ranging from warm blankets and hats on babies' heads, to more complex systems such as neonatal wraps and drapes and convection warmed incubators.

Neonatal wraps and drapes are particularly useful in preventing heat and moisture loss (insensible water loss) in infants. Known neonatal wraps provide access to the neonatal subject for examinations or medical procedures, and visual and auditory inspections of the neonatal subject. These wraps can also help seal the neonatal subject's transdermal diffusion, preventing moisture loss and appreciable drying of the subject, and often can be used with thermal radiation heaters used to keep the subject warm, or under phototherapy lamps, or during transport. The present disclosure addresses these issues, and methods and devices for enabling the routing of cabling, conduits, and similar devices into the wrap of the infant while maintaining appropriate heat and moisture levels.

SUMMARY OF THE DISCLOSURE

The present disclosure provides an improved neonatal drape device used to provide thermoregulation to a neonate. The neonatal drape device can be made of a single preformed sheet of non-static plastic material and can then be wrapped around an infant. Additionally, at various bend lines of the neonatal drape device, cutaways can align to provide notches, which further provide access points to the infant and enables routing of conduits and cables, while the infant remains wrapped by the neonatal drape device.

An aspect of an embodiment of the present disclosure provides a neonatal drape comprising a sheet formed from a pliable heat-retaining material. The sheet comprises a central base portion and at least one leaf separated from the central base by a fold line. The central base portion is sized and dimensioned to receive a neonatal subject in a supine position and the leaf is foldable over the neonatal subject along the fold line. At least one notch formed at a corner where the at least one leaf meets the base at the fold line, the at least one notch being sized and dimensioned to allow a conduit to extend from an internal space of the neonatal drape to an external location while the neonatal drape is wrapped around the neonatal subject.

The sheet can be made of a transparent plastic material, and can be made of a material that provides thermoregulation to the neonatal subject. The sheet can be comprised of a material that is repeatably self-adhesive as wrapped around the neonatal subject. The neonatal drape can include a plurality of leafs, and can include at least one leaf extending from a bottom of the base and at least one lateral leaf extending from a side of the base. The neonatal drape device can also comprise a slot formed in an outer edge. In some embodiments, the neonatal device can also include a bubble pack and a blanket. The bubble pack can be configured to have water flow into an inlet hose, through the bubble pack, and out of a drain hose, to control the temperature of water to aid in thermoregulation of the neonatal subject.

In another aspect, the present disclosure provides a neonatal drape comprising a sheet comprising a pliable material and including a base portion configured to receive a neonatal subject in a supine position and a plurality of leafs extending away from and separated from the base portion by fold lines and adapted to wrap around the neonatal subject to provide at least one of thermoregulation and moisture retention. A plurality of notches are formed at the corners where the plurality of leafs meet the base portion to enable routing of a conduit through the wrap.

The neonatal drape can be made of a transparent plastic material, thereby providing visibility to the neonatal subject. The sheet can be wrapped around the neonatal subject to provide a protective barrier and improving thermoregulation. At least one of the plurality of leafs can be a lateral leaf extending laterally from the base portion, and the lateral leaf comprises a separation line dividing the leaf into an upper lateral portion and a lower lateral portion. The plurality of leafs can also include a bottom leaf, extending from a lower edge of the base portion.

In another aspect of the disclosure, a method of protecting a neonatal subject is provided. The method comprises the steps of configuring a sheet of material adapted to provide thermoregulation to an infant to include a base portion sized and dimensioned to receive the infant in a supine position and a plurality of leafs extending from the base portion and separated from the base portion by fold lines, and forming a plurality of notches at the corners formed between the base portion and the leafs. The neonatal subject can be placed in a supine position on the base portion of the sheet, and wrapped with the sheet so as to conform the sheet to the neonatal subject. A portion of the sheet can be adhered to another portion of the sheet. At least one conduit can be routed from an internal location within the wrapped sheet to an external location through one of the plurality of notches. The conduit can be, for example, an electrical cable or an intravenous tube. A bubble pack can also be coupled to the base portion. A temperature-controlled fluid can be directed into an inlet hose, through the bubble pack, and out of a drain hose to aid in thermoregulation of the neonatal subject. A slot can be provided in an outer edge of each of right and left lateral leafs extending from the side edges of the base portion and in a bottom leaf extending from a lower edge of the base portion, the slots being centered in the leafs and positioned such that, when the neonatal subject is wrapped in the drape, the slots meet at a stump of the umbilical cord, and enable access to the stump.

These and other aspects of the disclosure will become apparent from the following description. In the description, reference is made to the accompanying drawings which form a part hereof, and in which there is shown a preferred embodiment of the disclosure. Such embodiment does not necessarily represent the full scope of the invention and reference is made therefore, to the claims herein for interpreting the scope.

DETAILED DESCRIPTION OF THE DISCLOSURE

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 1:
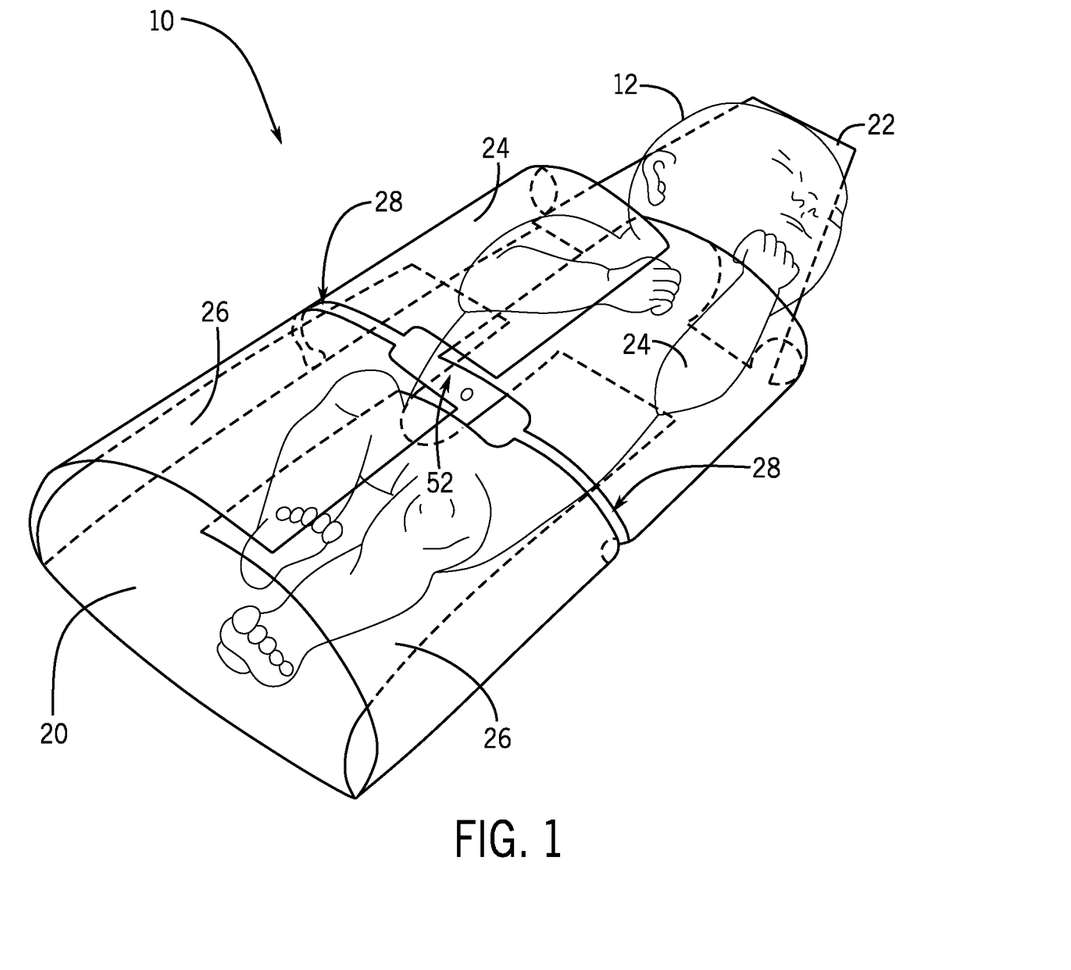
FIG. 1 is a front, right, top perspective view of a neonatal drape device, wrapped around an infant.

The present disclosure describes a neonatal drape device. FIG. 1 illustrates a neonatal drape device 10, according to one embodiment of the disclosure. In some embodiments, the neonatal drape device 10 can be used to reduce heat and insensible evaporative water loss of a neonatal subject or an infant 12. For example, the neonatal drape device 10 can be used to reduce heat loss of a prematurely born infant 12 while the infant 12 is being transported to an incubator, or in other settings. The neonatal drape device 10 can be advantageously used to reduce heat loss of an infant 12 while providing a passageway for cables, conduits and other devices to extend from an interior location within the neonatal drape device 10 to an exterior location for connection to external supplies, equipment, or other devices such as fluids, electrical power, monitoring devices, heating or cooling elements, and other devices.

Figure 2:
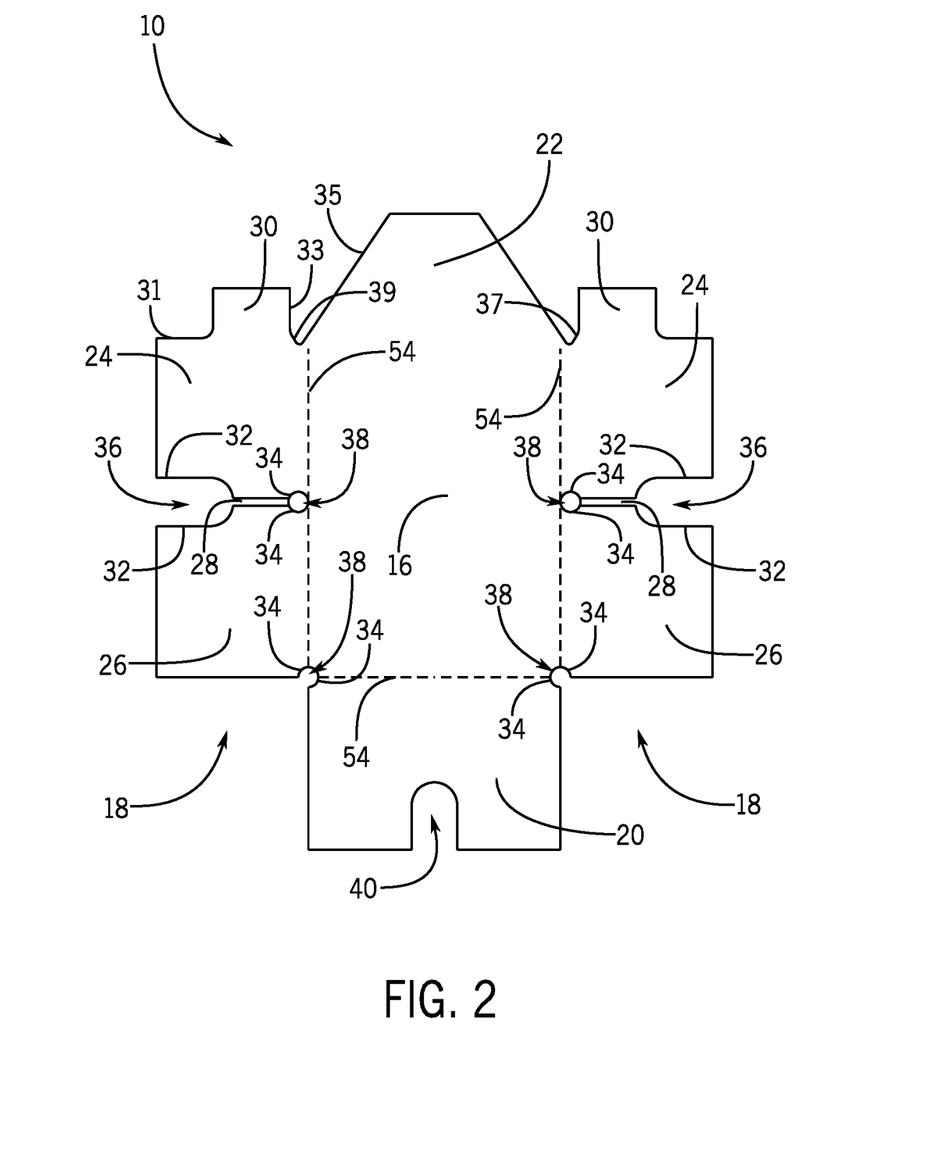
FIG. 2 is a plan view of the neonatal drape device of FIG. 1, shown in an unfolded configuration.

As illustrated in FIGS. 1 and 2, the neonatal drape device 10 comprises a sheet material which can be cut or otherwise formed to provide a predetermined shape that can be folded to wrap an infant. As shown here, the neonatal drape 10 comprises a central base 16, right and left lateral leaves 18, and a foot or bottom leaf 20. The base 16 defines a substantially rectangular shape sized and dimensioned to receive a neonate or infant and includes a trapezoidal-shaped projection 22 projecting from a head or top edge of the base 16. The two lateral leaves 18 are each connected to and extend from two lateral edges of the base 16, separated by a bend or fold line 54. Each of the two lateral leaves 18 are further bisected into an upper lateral portion 24 and a lower lateral portion 26 by a separation line 28. The foot or bottom leaf 20 is similarly adjacent to and separated from the base 16 by a fold line 54. As shown in FIG. 1, and as described more fully below, the base 16 is sized and dimensioned to receive an infant or neonate, and the upper projection 22 can be folded onto the infant's head, the foot leaf 20 folded up over the infant's feet, and the lateral side leaves 18 are foldable over the infant's body, as described more fully below. The right and left lateral side leaves are mirror images of one another, and will be described together below.

The upper lateral portion 24 of each of the two lateral leaves 18 includes a top projection 30, which projects from an upper edge 31 of the upper lateral portion 24. A vertical internal edge 33 of the top projection 30 is located adjacent the top of the fold line 54 between the lateral leave 18 and the base 16, and adjacent an upwardly-angled edge 35 forming the upper trapezoidal-shaped projection 22 of the base 16. The intersection of the vertical internal edge 33 of the top projection 30 and the angled edge 33 the upwardly-angled edge of the base 16 defines a triangular notch 39. As shown here, the vertical internal edge 33 extends below the horizontal upper edge 31 of the lateral leaf 18, and is horizontally offset from the fold line 34 to provide a relatively large notch 39. A similar notch 37 is provided on the opposing side of the projection 22.

The upper lateral portion 24 further includes a slot cutaway 32 and a notch cutaway 34, both disposed along a bottom edge of the upper lateral portion 24 adjacent the separation line 28. The slot cutaway 32 is disposed at an outer end of the separation line 28 and the notch cutaway 34 is disposed at an inner end of the separation line 28. The lower lateral portion 26 of each of the two lateral leaves 18 includes a similar slot cutaway 32 and a notch cutaway 34 disposed along a top edge of the lower lateral portion 26 adjacent the separation line 28 forming mirror images of the slot 32 and notch 34 in the upper lateral portion, with the slot cutaway 32 disposed at the outer end of the separation line 28 and the first notch cutaway is disposed at the inner end of the separation line 28. An additional notch cutaway 34 of the lower lateral portion 26 is disposed along a bottom edge of the lower lateral portion 26 adjacent the base 16. As seen in FIG. 2, this notch 34 mates with similar notches formed in a lower corner of the base 16 and an upper corner of the bottom or foot portion 20 to form a circular opening where the fold lines 54 separating the base from the lateral leaf 18 and bottom leaf 20 meet on both sides of the base 16.

As described above, the slot cutaways 32 of the upper and lower lateral portions 24, 26 are disposed adjacent to one another, effectively forming an outer slot 36 on each of the two lateral leaves 18. Similarly, the notch cutaway 34 of the upper lateral portion 24 and the first of the two notch cutaways 34 of the lower lateral portion 26 are disposed adjacent to one another, effectively forming a notch 38 on each of the two lateral leaves 18. The separation line 28 forms a channel between the outer slot 36 and inner notch 34.

With continued reference to FIGS. 1 and 2, the bottom leaf 20 is disposed along a bottom edge of the base 16 and includes a slot 40 and two notch cutaways 34. The slot 40, as shown here, can be centered between the two side edges of the bottom leaf 20, and cut or formed into a bottom edge of the bottom leaf 20. The two notch cutaways 34 of the bottom leaf 20 are disposed at upper corners of the bottom leaf 20 and are additionally disposed adjacent to the second of the two notch cutaways 34 of each of the lower lateral portions 26, effectively forming notches 38 disposed at bottom corners of the base 16, as described above.

Figure 3:
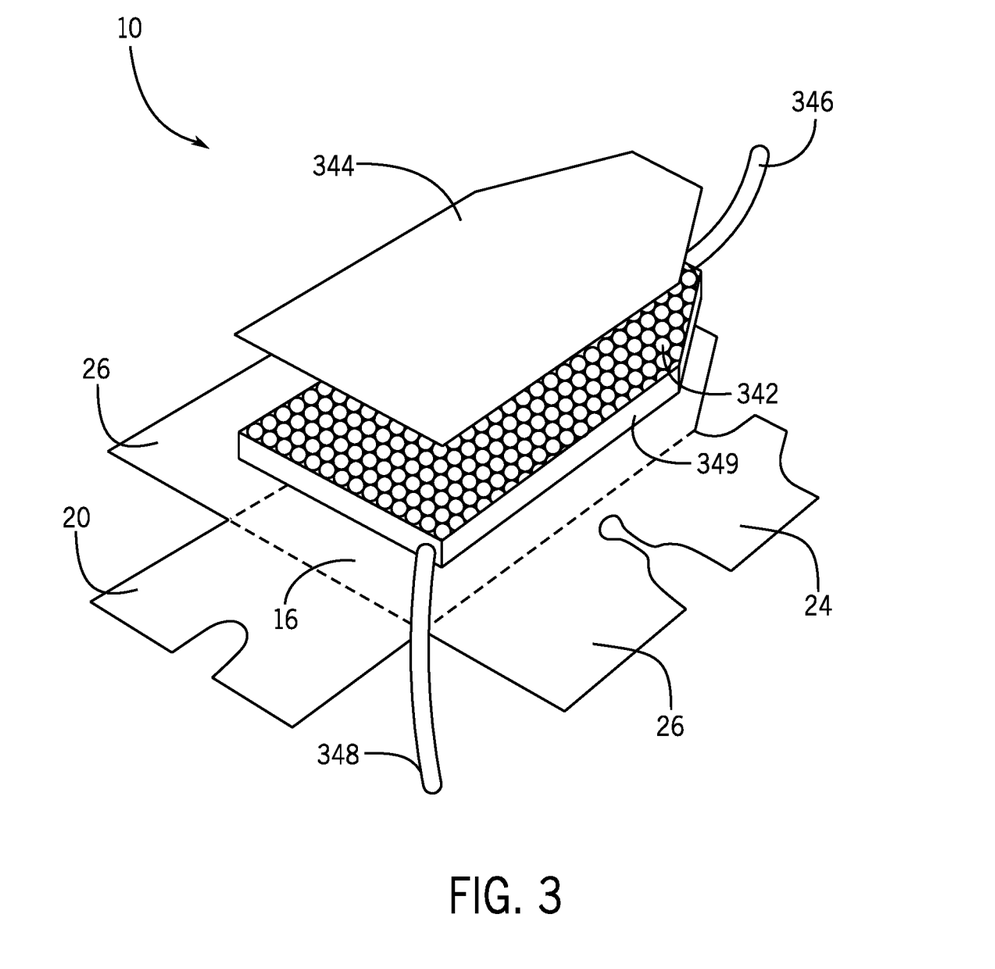
FIG. 3 is a front, right, top exploded perspective view of the neonatal drape device of FIG. 1, shown with a bubble pack and a blanket.

Turning now to FIG. 3, the neonatal drape device 10 can additionally include a bubble pack 342 coupled to a top surface of the base 16 and a blanket 344 coupled to a top surface of the bubble pack 342. Both the blanket 344 and the bubble pack 342 can be configured to have the same general shape as the base 16. In some embodiments, the bubble pack 342 can also include an inlet hose 346 and a drain hose 348. The inlet hose 346 and the drain hose 348 can further be collectively configured to allow liquid to flow through the bubble pack 342, as will be described in detail below. Additionally, the bubble pack 342 may also be enveloped or partially enveloped by a space blanket 349, which may comprise a Mylar sheet or other materials such as low density (LDPE), low linear density (LLDPE) polyurethane or polyvinylchloride, or another translucent transdermal diffusion barrier. In some embodiments, the blanket 344 may be comprised of a quilted fabric, heat conservation cushion, or other insulating material. Furthermore, in some embodiments, the neonatal drape device 10 can include the bubble pack 342, blanket 344, or space blanket 349 together or individually, and all combinations of these elements are contemplated by the current disclosure.

Figure 4:
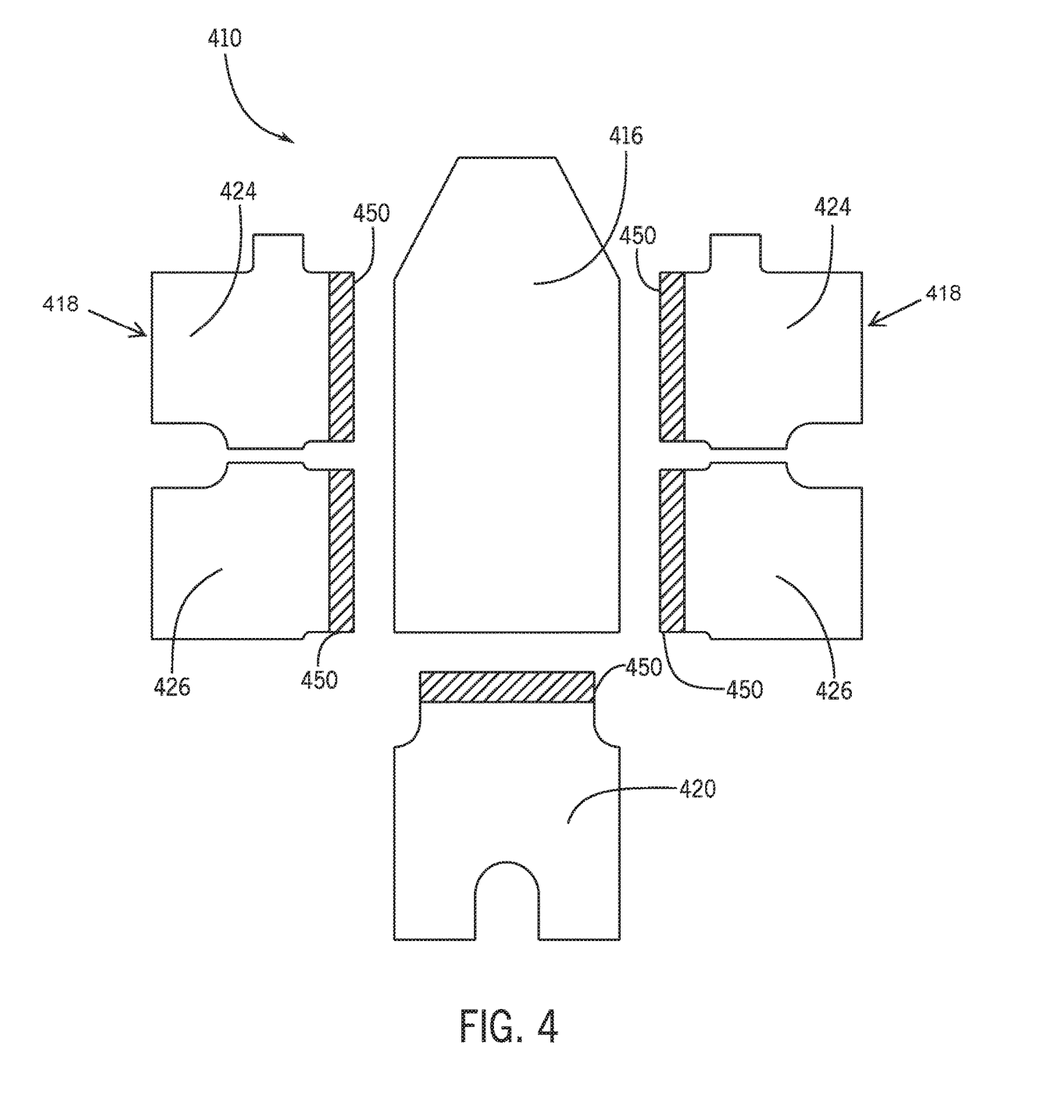
FIG. 4 is a plan exploded view of a neonatal drape device.

With reference now to FIG. 4, a neonatal drape device 410 is illustrated according to another embodiment of the disclosure. The neonatal drape device 410 is similar to the neonatal drape device 10 except that the upper and lower lateral portions 424, 426 of each of the two lateral leaves 418, as well as the bottom leaf 420, are formed separate pieces as or can be fully separated from the base 416. Each of the lateral portions 424, 426 as well as the bottom leaf 420 additionally include an attachment portion 450 configured to repeatably and detachably couple each of the lateral portions 424, 426, as well as the bottom leaf 420, to the base 416. Attachment can be made, for example, using pins, adhesives, hook and loop type fasteners or other adhering devices and methods. The notches, slots, and channels formed in the drape device 410 can be similarly closed with detachable covers (not shown) that can enclose the openings when not in use.

Now that the general structure of the neonatal drape device 10 (and the neonatal drape device 410) has been described above, an exemplary method of manufacturing the neonatal drape device 10 will be described below. It should be understood that the neonatal drape device 10 can be manufactured according to a wide variety of methods, and the following description is not meant to be limiting.

In one embodiment, the neonatal drape device 10 can be made of a non-static, pliable, thin sheet material that is repeatedly self-adhesive due to characteristics of the material and capable of being folded around an infant while providing insulation to warm and maintain moisture. The sheet cut into the general shape of the neonatal drape device 10, as best illustrated in FIG. 2. In some embodiments, such as the embodiment illustrated in FIG. 4, when the two lateral leaves 418 and the bottom leaf 420 are provided separate from the base 416, each of the individual pieces can be made of the sheet material and cut into their corresponding general shapes. After the individual pieces are formed, they are then coupled together to form the neonatal drape device 410. This coupling can be done through any of a reusable adhesive, buttons, snaps, Velcro, diaper-like tabs or any other suitable coupling method. In either embodiment, the sheet material can be plastic or other materials such as an insulating occlusive skin wrap (i.e. "space blanket material").

In some embodiments, the sheet material is made of plastic, and may be approximately 0.003 inches in thickness. In other embodiments, the plastic sheet material may be between 0.001 inches and 0.008 inches in thickness depending on intended use to achieve various desired results. In a preferred embodiment, the plastic sheet material may be transparent in order to provide total visibility of the infant 12 while the infant 12 is wrapped within the neonatal drape device 10, as will be described below.

Additionally, in some embodiments that include the bubble pack 342, the blanket 344, and the space blanket 349, the space blanket 349 may first be wrapped around and coupled to the bubble pack 342. Subsequently, the bubble pack 342, either fully or partially enveloped by the space blanket 349, can be coupled to the base 16 of the neonatal drape device 10 (or the neonatal drape device 410). Finally, the blanket 344 can be placed over the bubble pack 342 and coupled thereto. The couplings between the space blanket 349, the bubble pack 342, the blanket 344 and the base 16 (or the base 416) can be achieved through any of an adhesive, heat welding, snaps, hook and loop fasteners, or any other suitable coupling method.

Now that both the general structure and an exemplary method of manufacturing the neonatal drape device 10 has been described above, the functionality of the neonatal drape device 10 will be described below. Again, it should be understood that the neonatal drape device 10 can be used in a wide variety of settings to achieve a multitude of desired results, and the following description is not meant to be limiting.

As described above, during use, the infant 12 is placed on the base 16 of the neonatal drape device 10 in a supine position, such that the head of the infant 12 rests on the trapezoidal-shaped upper projection 22. Once the infant 12 is placed onto the base 16, the two lateral leaves 18, including the upper and lower lateral portions 24, 26, as well as the bottom leaf 20, are then wrapped around the infant 12 by bending the various leaves 18, 20 around bend or fold lines 54. The various leaves 18, 20 in the illustrated embodiment may be held in place by the self-adhesion properties of the plastic sheet material. Additionally, the various leaves 18, 20 can be detachably coupled around the infant 12 through the use of hook and loop fasteners, adhesives, tape, pins, snaps, buttons, or any other suitable coupling method. The various leaves 18, 20 thereby provide a protective barrier around the infant 12, effectively improving thermoregulation by reducing the various modes of heat transfer away from the infant 12 (i.e., conduction, radiation, convection, or evaporation), while concurrently providing visibility to the infant 12. This allows doctors, physicians, etc., to visually assess the infant 12 with less risk of a drop in the body temperature of the infant 12, which, as previously stated, has been linked to higher mortality rates.

Additionally, the outer slots 36 formed by the slot cutaways 32 of the upper and lower portions 24, 26 of the two lateral leaves 18 collectively form an access hole 52 when the infant 12 is wrapped within the neonatal drape device 10. The access hole 52 can be used by a doctor, physician, etc., to access the umbilical stump or midsection of the infant 12. Similarly, the notches 38 between the bottom leaf 20 and the lower lateral portions 26, as well as the notches 38 between the upper and lower lateral portions 24, 26, provide access to the infant 12 while the infant 12 is wrapped within the neonatal drape device 10. The notches 38 and 39 can be used by a doctor, physician, etc., to route various cables and medical tools from an internal location within the wrapped neonatal drape device 10 to an external location, such as, for example, an intravenous line providing medication to the infant 12, various vascular sensors for monitoring the vascular health of the infant 12, various temperature probes for monitoring the body temperature of the infant, or any other necessary cables or medical tools that may be used to monitor or treat the infant 12.

In some embodiments, where the neonatal drape device 10 includes the bubble pack 342 with the inlet hose 346 and the drain hose 348, temperature controlled water (or another suitable fluid) can be pumped through the bubble pack 342 to aid in maintaining the body temperature of the infant 12. Temperature probes, as described above, may be connected to a processing device, which may, in turn, control a water flow to feed warmer or cooler water through the bubble pack 342 to maintain the body temperature of the infant 12 within a predetermined temperature window.

Figure 5:
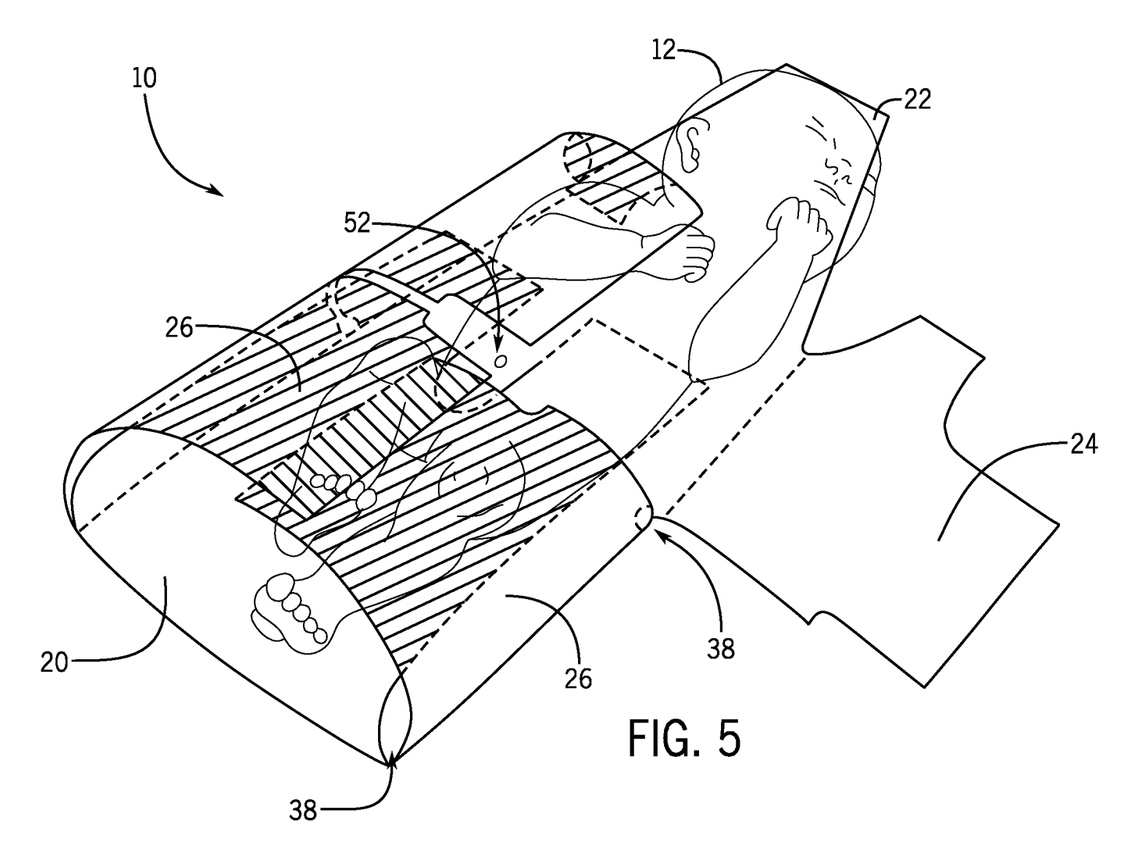
FIG. 5 is a front, right, top perspective view of the neonatal drape device, wrapped around an infant, with an upper portion of a lateral leaf unfolded.

Turning now to FIG. 5, any of the upper and lower portions 24, 26 of the two lateral leaves 18 can be unwrapped to provide further access to the infant 12. In some embodiments, this may be done when the access hole 52 and the notches 38 don't provide the necessary accessibility to the infant 12. Additionally, the unwrapping of the various leaf portions 24, 26 can further be used to situate the various cables within the neonatal drape device 10, which can then be routed from the internal location within the neonatal drape device 10 to the external location, as described above. In some embodiments, such as the embodiment illustrated in FIG. 4, where the various leaves 418, 420 are detachably coupled to the base 416, instead of simply unwrapping the various leaves 418, 420, they can be temporarily removed from the neonatal drape device 410 to remove unnecessary viewing obstruction of the infant 12. Then, once the doctor, physician, etc., no longer needs access to the infant 12, the various leaves 418, 420 can be reattached to the base 416. The selective use of leaf opening allows access to the body of the infant across selected folded portions, while maximizing thermal and moisture control.

Figure 6:
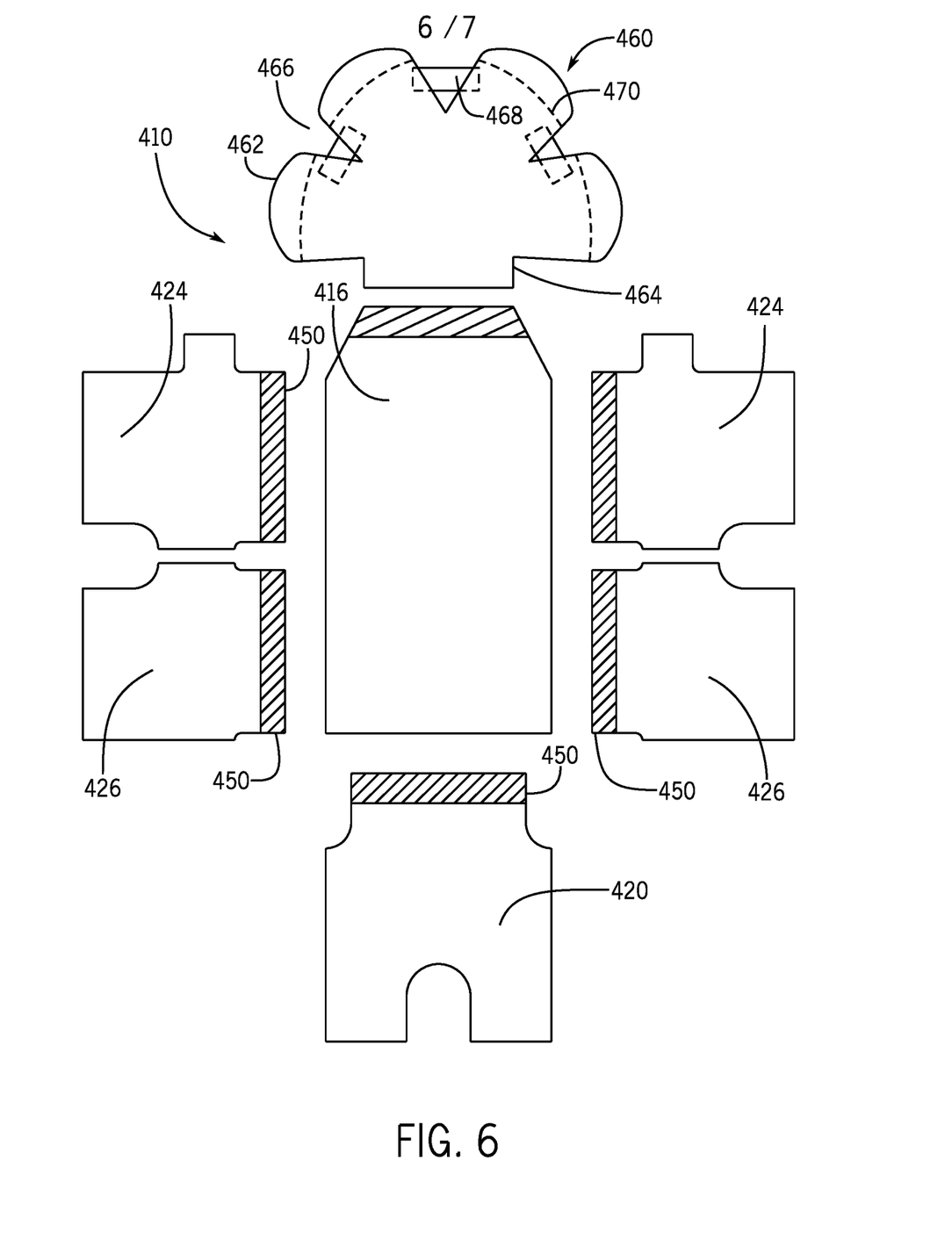
FIG. 6 is a plan exploded view of another embodiment of a neonatal drape device.
Figure 7:
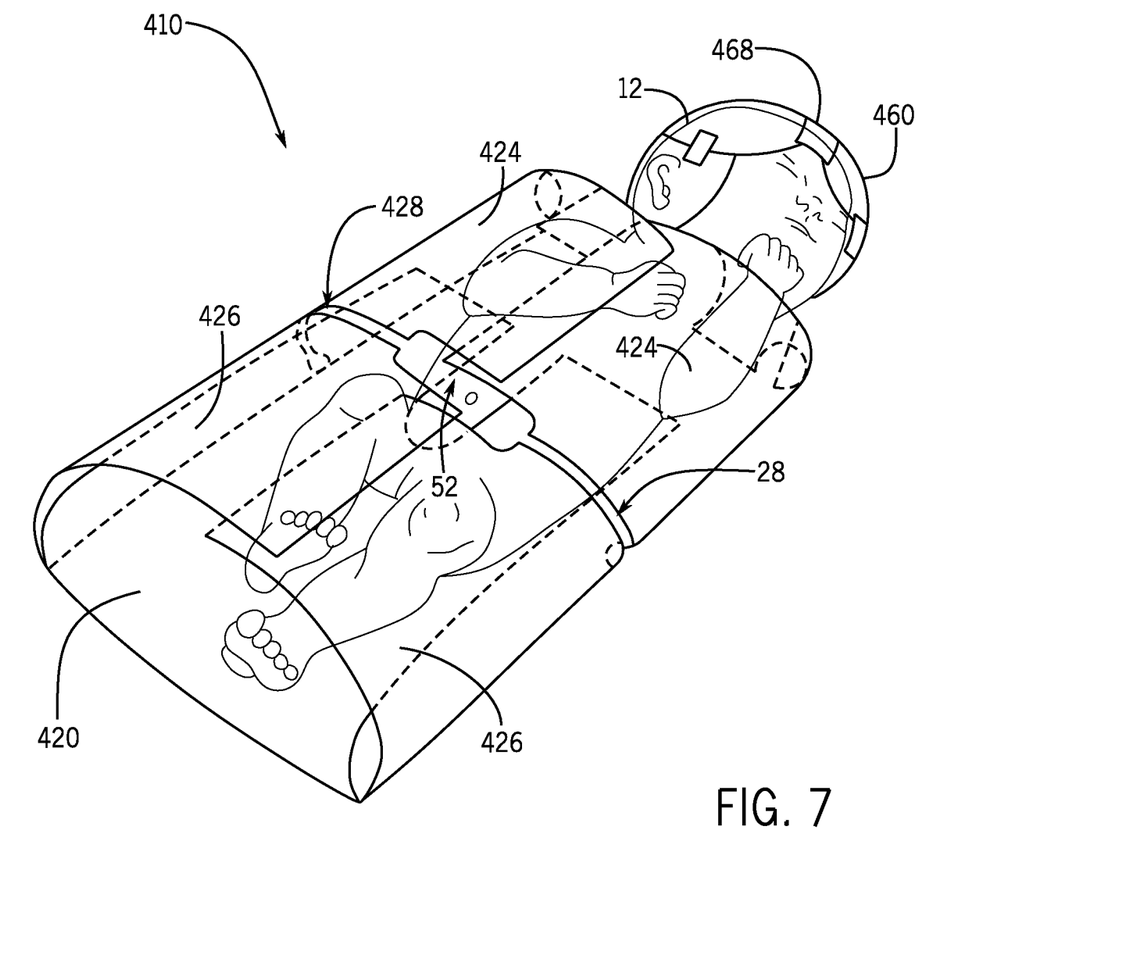
FIG. 7 is a front, right, top perspective view of a neonatal drape device of the type shown in FIG. 6, wrapped around an infant.

Referring now to FIGS. 6 and 7, an alternate embodiment of neonatal drape device 410 is shown. Here, the device includes a detachable hood 460 that can include, as shown, a semi-circular hood with a plurality of circumferential hood leaves 462 or "petals" circumventing the hood, the leaves 462 separated from one another by slits or notches 466. The slits or notches can be selectively folded or closed using enclosure tabs 468 which can be similar to diaper tabs extending across the notches 466. The hood leaves 462 can be selectively folded and pleated back, as shown by fold line 470, to fit the hood 460 to a smaller head. The slits or notches 466 are sized to enable cables for sensors, monitoring equipment, or fluids, such as cranial IVs, to be routed to the head of the infant 12. A mounting tab 464 extends from the bottom end of the hood 460 to enable connection to the base 416. The mounting tab 464 and enclosure tables 468 can be constructed from hook and loop fasteners, adhesives, tape, pins, snaps, buttons, or any other suitable coupling method. Although a semi-circle is shown here, various geometric shapes that can encompass the head, including ovals, polygons of various types, triangles, and other shapes can also be used as a hood 460. Further, although the hood 460 is shown as a separate element, a similar hood could be integral with the neonatal drape, similar to the trapezoidal-shaped projection 22 described above.

Although specific embodiments are described above, it will be apparent to those of ordinary skill that a number of variations can be made within the scope of the disclosure. For example, it will be apparent that the shapes of the described leaves can be varied. While a trapezoidal-shaped element is shown extending from the base 16, this element can be triangular, rectangular, square, or in other shapes. This upper portion of the base can also be formed as a separate leaf. The generally rectangular base and leaves shown here can also be formed in different geometric shapes, including squares, triangles, trapezoids, and various other polyhedrons, as well as other types of rounded shapes. Various types of sheet and heating materials can be used, as described above. In some embodiments, the neonatal drape device 10 may also be provided with additional or fewer "leaves". Additional leaves could further provide additional notches between said leaves, thereby providing for more cables and wires to be routed from an internal location within the neonatal drape device 10 to an external location. Furthermore, the two lateral leaves 18 may alternatively be single pieces that are not bisected into upper and lower lateral portions 24, 26. Although notches, channels, and slots are shown in the drawings, it will be apparent that the size of these openings could be modified depending on the type of cable, conduit, or device that is intended to be routed to the infant. Further, the notches, channels, and slots are not restricted to any particular shape. These elements can be generally circular, triangular, oval, rectangular, or different shapes. It should be understood, therefore, that the methods and apparatuses described above are only exemplary and do not limit the scope of the invention, and that various modifications could be made by those skilled in the art that would fall within the scope of the invention. To apprise the public of the scope of this invention, the following claims are made:

I claim:

1. A neonatal drape device comprising:
   a sheet formed from a pliable heat-retaining material and comprising a central base portion having a length and a width and at least one lateral leaf separated from the central base portion by a fold line extending along a side edge of the central base portion along the length and having a length dimension substantially equivalent to the entire length dimension of the central base portion and at least one bottom leaf separated from the central base portion by a fold line, the bottom leaf having a width dimension substantially equivalent to the width dimension of the central base portion, the central base portion sized and dimensioned to receive a neonatal subject in a supine position and the at least one bottom leaf foldable over the neonatal subject along the fold line; and at least one notch formed as a cutaway in an edge of the pliable heat-retaining material forming the sheet at a corner where at least one of the lateral leaf and the bottom leaf meets the central base portion at the fold line, the at least one notch being sized and dimensioned to allow a conduit to extend from an internal space of the neonatal drape to an external location while the neonatal drape is wrapped around the neonatal subject.

2. The neonatal drape device of claim 1, wherein the sheet is made of a transparent plastic material.

3. The neonatal drape device of claim 1, wherein the sheet is made of a material that provides thermoregulation to the neonatal subject.

4. The neonatal drape device of claim 1, wherein the at least one leaf comprises a slot formed in an outer edge.

5. The neonatal drape device of claim 1, further comprising a bubble pack and a blanket.

6. The neonatal drape device of claim 5, wherein the bubble pack includes an inlet hose and a drain hose.

7. The neonatal drape device of claim 6, wherein the bubble pack is configured to have water flow into the inlet hose, through the bubble pack, and out of the drain hose, the water being temperature controlled to aid in thermoregulation of the neonatal subject.

8. The neonatal drape device of claim 1, wherein the sheet is comprised of a material that is repeatedly self-adhesive.

9. The neonatal drape device of claim 1, wherein one of the plurality of leaves comprises a semi-circular hood, the semi-circular hood comprising a plurality of slits sized and dimensioned to enable routing of cables through the hood.

10. A neonatal drape device comprising:
a sheet comprising a pliable material and including a central base portion having a length dimension and a width dimension and configured to receive a neonatal subject in a supine position and a plurality of leaves extending away from the central base portion and adapted to wrap around the neonatal subject, the plurality of leaves comprising a lateral leaf and a bottom leaf, the lateral leaf extending from a side edge of the central base portion and having a length substantially equivalent to the entire length dimension of the central base portion and the bottom portion extending from a bottom edge of the central base portion, and having a width substantially equivalent to the width dimension of the central base portion; and
a notch formed as a cutaway in the pliable material of the sheet at a corner of the central base portion where the lateral leaf, the bottom leaf, and the central base portion meet to enable routing of a conduit through the neonatal drape device.

11. The neonatal drape device of claim 10, wherein the sheet is made of a transparent plastic material.

12. The neonatal drape device of claim 10, wherein the leaves are coupled to and repeatedly separable from the base portion.

13. The neonatal drape device of claim 10, wherein the lateral leaf comprises a separation line dividing the lateral leaf into an upper lateral portion and a lower lateral portion.

14. A neonatal drape device comprising:
a central base portion comprising a pliable material and having a side edge defined by a length dimension and a bottom edge defined by a width dimension, the central base portion configured to receive a neonatal subject in a supine position;
a plurality of leaves, each comprising a pliable material and configured to be connected to the central base portion, the plurality of leaves adapted to wrap around the neonatal subject, the plurality of leaves comprising a lateral leaf configured to extend along the entire side edge of the central base portion along the length dimension, and a bottom leaf configured to extend along the bottom edge of the central base portion along the width dimension; and
a first notch formed as a cutaway in an edge of the pliable material forming the central base portion, a second notch formed as a cutaway in the pliable material forming the lateral leaf, and a third notch formed as a cutaway in the pliable material forming the bottom leaf, wherein the first, second, and third notches align to form a conduit notch adjacent a corner where the central base portion, the lateral leaf, and the bottom leaf meet, the conduit notch being sized and dimensioned to allow a conduit to extend from an internal space of the neonatal drape to an external location while the neonatal drape is wrapped around the neonatal subject.

15. The neonatal drape device of claim 14, wherein the plurality of leaves are integral with the central base portion.

16. The neonatal drape device of claim 14, wherein the plurality of leaves are removably connected to the central base portion.

17. The neonatal drape device of claim 14, wherein the plurality of leaves are connected to the base portion with at least one of an adhesive, a hook and loop type fastener, a pin, a button, or a snap.

18. The neonatal drape device of claim 14, further comprising a hood extending from an end of the central body portion opposite the bottom edge.

19. The neonatal drape device of claim 18, wherein the hood comprises at least one slit extending from an outer edge toward an interior of the hood.

20. The neonatal drape device of claim 14, wherein the conduit notch comprises at least a portion of a circular shape.

* * * * *